United States Patent
Hinds

(10) Patent No.: US 9,925,083 B2
(45) Date of Patent: Mar. 27, 2018

(54) WRIST BRACE

(71) Applicant: 3M INNOVATIVE PROPERTIES COMPANY, St. Paul, MN (US)

(72) Inventor: Sherry A. Hinds, Goshen, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/149,431

(22) Filed: Jan. 7, 2014

(65) Prior Publication Data

US 2014/0121579 A1    May 1, 2014

Related U.S. Application Data

(63) Continuation of application No. 13/256,257, filed as application No. PCT/US2010/029127 on Mar. 30, 2010, now abandoned.

(60) Provisional application No. 61/165,320, filed on Mar. 31, 2009.

(51) Int. Cl.
*A61F 5/01* (2006.01)
*A61F 5/058* (2006.01)

(52) U.S. Cl.
CPC ............ *A61F 5/013* (2013.01); *A61F 5/0118* (2013.01); *A61F 5/05858* (2013.01); *A61F 5/05866* (2013.01)

(58) Field of Classification Search
CPC .. A61F 5/00; A61F 5/01; A61F 5/0118; A61F 5/013; A61F 5/058; A61F 5/05858; A61F 5/05866
USPC ............................ 602/20, 21, 23, 27, 64, 65
See application file for complete search history.

(56) References Cited

U.S. PATENT DOCUMENTS

| | | | |
|---|---|---|---|
| 851,950 | A | 4/1907 | Le Mat |
| 1,027,897 | A | 5/1912 | Quenzer |
| 1,037,441 | A | 9/1912 | Collis |
| 1,081,366 | A | 12/1913 | Collis |
| 3,028,861 | A | 4/1962 | Shapiro |
| 3,298,365 | A | 1/1967 | Lewis |
| 3,970,083 | A | 7/1976 | Carrigan |
| 4,187,844 | A | 2/1980 | Caprio, Jr. |

(Continued)

FOREIGN PATENT DOCUMENTS

| | | |
|---|---|---|
| EP | 820741 | 1/1998 |
| JP | 3072845 | 11/2000 |

(Continued)

OTHER PUBLICATIONS

International Search Report for PCT/US2010/029127, dated Nov. 10, 2010, 3 pages.

(Continued)

*Primary Examiner* — Keri J Nelson
(74) *Attorney, Agent, or Firm* — Sandra K. Nowak

(57) ABSTRACT

A wrist brace comprises (a) a main brace body, (b) an adjustable wrist strap configured to encircle the main brace body about a wearer's wrist, and (c) a lace and rotatable tightening mechanism. The main brace body comprises a semi-rigid splint configured to fit the anterior of a wearer's wrist, extending from the palm to a portion of the anterior of the forearm. The lace and tightening rotatable mechanism is configured to apply tension on the lace thereby tightening the wrist strap about the wearer's wrist and drawing the splint closer to the anterior of the wearer's wrist.

15 Claims, 4 Drawing Sheets

(56) References Cited

U.S. PATENT DOCUMENTS

| | | | |
|---|---|---|---|
| 4,237,874 A | 12/1980 | Nelson | |
| 4,280,488 A | 7/1981 | Polsky | |
| 4,527,556 A | 7/1985 | Nelson | |
| 4,651,726 A | 3/1987 | Holland | |
| 4,716,892 A | 1/1988 | Brunswick | |
| 4,724,847 A | 2/1988 | Nelson | |
| 4,825,856 A | 5/1989 | Nelson | |
| 4,854,309 A * | 8/1989 | Elsey | A61F 5/0118 602/21 |
| 4,878,504 A | 11/1989 | Nelson | |
| 4,936,295 A | 6/1990 | Crane | |
| 4,960,135 A | 10/1990 | Nelson | |
| 5,000,195 A | 3/1991 | Neal | |
| 5,007,417 A | 4/1991 | Bender | |
| 5,014,691 A | 5/1991 | Cueman | |
| 5,160,314 A | 11/1992 | Peters | |
| 5,356,371 A | 10/1994 | Hubbard | |
| 5,657,767 A | 8/1997 | Nelson | |
| 5,681,271 A | 10/1997 | Nelson | |
| D388,173 S | 12/1997 | Eriksson | |
| 5,741,222 A | 4/1998 | Fiore | |
| D394,112 S | 5/1998 | Duback | |
| 5,769,804 A | 6/1998 | Harris | |
| 5,795,316 A | 8/1998 | Gaylord | |
| 5,853,381 A | 12/1998 | Stevenson | |
| 5,868,693 A | 2/1999 | Duback | |
| 5,944,678 A | 8/1999 | Hubbard | |
| 6,155,997 A | 12/2000 | Castro | |
| 6,200,286 B1 | 3/2001 | Zamani | |
| 6,394,971 B1 | 5/2002 | Slautterback | |
| 6,398,750 B1 | 6/2002 | Quinn | |
| 6,540,705 B2 | 4/2003 | Norstrem | |
| 6,602,215 B1 | 8/2003 | Richie | |
| 6,652,474 B1 | 11/2003 | Quinn | |
| 6,663,583 B1 | 12/2003 | Janis | |
| 6,790,238 B1 * | 9/2004 | Martin | 623/36 |
| 6,893,410 B1 * | 5/2005 | Hely | 602/21 |
| 7,014,621 B2 | 3/2006 | Nelson | |
| 7,056,298 B1 * | 6/2006 | Weber | A61F 5/0118 2/16 |
| 7,175,603 B2 * | 2/2007 | Fritsch | A61F 5/0118 2/16 |
| D552,744 S | 10/2007 | Verkade | |
| 7,497,839 B2 | 3/2009 | Quinn | |
| 7,651,472 B2 | 1/2010 | Gaylord | |
| 7,716,892 B2 | 5/2010 | Kim | |
| D639,965 S | 6/2011 | Wehsely-Swiczinsky | |
| D649,651 S | 11/2011 | Weaver | |
| 2003/0114782 A1 * | 6/2003 | Chiang et al. | 602/6 |
| 2004/0049141 A1 * | 3/2004 | Slautterback | A61F 5/0118 602/21 |
| 2005/0197609 A1 * | 9/2005 | Mills | 602/21 |
| 2006/0004310 A1 | 1/2006 | Parizot | |
| 2006/0004311 A1 | 1/2006 | Hargrave | |
| 2006/0052734 A1 | 3/2006 | Evans | |
| 2006/0069335 A1 | 3/2006 | Fritsch | |
| 2006/0156517 A1 | 7/2006 | Hammerslag | |
| 2007/0169378 A1 | 7/2007 | Sodeberg | |
| 2007/0239093 A1 * | 10/2007 | Wyatt | A61F 5/0118 602/21 |
| 2008/0039765 A1 | 2/2008 | Nordt, II | |
| 2008/0066272 A1 | 3/2008 | Hammerslag | |
| 2008/0249448 A1 * | 10/2008 | Stevenson | A61F 5/0125 602/16 |
| 2011/0144554 A1 | 6/2011 | Weaver | |

FOREIGN PATENT DOCUMENTS

| | | |
|---|---|---|
| KR | 10-2007-0078568 | 8/2007 |
| WO | WO 2005-087150 | 9/2005 |
| WO | WO 2007-051524 | 5/2007 |
| WO | WO 2008-033963 | 3/2008 |
| WO | WO 2009-140165 | 11/2009 |
| WO | WO 2010-117723 | 10/2010 |

OTHER PUBLICATIONS

Written Opinion for PCT/US2010/029127, dated Nov. 10, 2010, 3 pages.

* cited by examiner

WRIST BRACE

CROSS REFERENCE TO RELATED APPLICATIONS

This application is continuation of application Ser. No. 13/256,257, filed Mar. 30, 2010, which claims priority to a national stage filing under 35 U.S.C. 371 of PCT/US2010/029127, filed Mar. 30, 2010, which claims priority to Provisional Application No. 61/165,320, filed Mar. 31, 2009, the disclosure of which is incorporated by reference in its/their entirety herein.

FIELD

This invention relates to a wrist brace having an adjustable wrist strap.

BACKGROUND

Many people suffer from injury to the soft tissues of the wrist and carpal tunnel, which is often caused by frequent, sustained repetitive motion involving the hands. Carpal tunnel syndrome (CTS), or median neuropathy at the wrist, is a medical condition in which the median nerve is compressed at the wrist leading to paresthesias (a sensation of tingling or prickling), numbness, and/or muscle weakness in the hand.

Applying a splint or brace to the wrist can help limit the symptoms of CTS by limiting wrist flexion and maintaining the wrist in neutral position. Numerous splints and braces have therefore been developed for treatment of CTS. Such braces are typically secured to the hand and wrist using laces, buckles, and/or hook and loop closures (for example, Velcro™). But, wrist splints and braces comprising these types of closure systems tend to lose tension or loosen over time during use. For example, buckles can slide, laces can elongate, and hook and loop closures can loosen. This is especially a problem at the bend or break in the wrist where extra support is needed to maintain the hand/wrist in neutral position.

SUMMARY

In view of the foregoing, we recognize that there is a need in the art for wrist braces for treating CTS that hold the hand/wrist in neutral position and do not loosen over time during use, especially at the bend or break in the wrist. In addition, we recognize that it would be advantageous if such wrist braces could be quickly loosened and retightened so that, depending upon the desired level of compression desired, the user could adjust the wrist brace accordingly.

Briefly, in one aspect, the present invention provides a wrist brace comprising (a) a main brace body, (b) an adjustable wrist strap configured to encircle the main brace body about a wearer's wrist, and (c) a lace and rotatable tightening mechanism. The main brace body comprises a semi-rigid splint configured to fit the anterior of a wearer's wrist, extending from the palm to a portion of the anterior of the forearm, disposed at least partially within the main brace body. The lace and rotatable tightening mechanism is configured to apply tension on the lace thereby tightening the wrist strap about the wearer's wrist and drawing the splint closer to the anterior of the wearer's wrist.

The wrist braces of the present invention meet the need in the art for wrist braces for treating CTS that hold the hand/wrist in neutral position and do not loosen over time during use. The adjustable wrist strap can be tightened to provide extra support at the break in the wrist. In addition, the lace and rotatable tightening mechanism enables the wearer to quickly and easily loosen and retighten the adjustable strap as needed.

DETAILED DESCRIPTION

Figure 1:
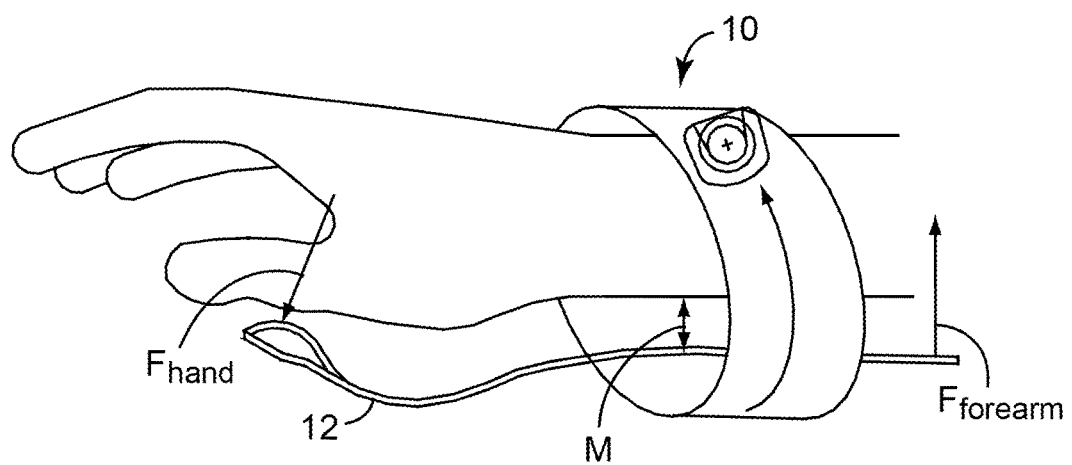
FIG. 1 schematically illustrates the use of an adjustable wrist strap.

The wrist braces of the present invention include a main brace body with a semi-rigid splint disposed at least partially therein. The main brace body can be constructed of one tube-like piece with a large hole for all of the wearer's fingers and a smaller hole for the wearer's thumb. Such a main brace body could be applied to a wearer's hand and wrist in a fashion similar to pulling on a glove. Typically, however, the main brace body is formed from a single piece that wraps around the wearer's wrist and hand, forming two ends with opposing sides that are drawn towards each other (or possibly even overlap) on the posterior of the wearer's wrist and hand when the wrist brace is applied. Some embodiments also include a tongue portion. The main brace body can be secured across the tongue portion using conventional securing means or a reel and lace system as described below. In some embodiments, the tongue is completely removable from the brace. In some embodiments, the tongue may be configured such that it allows complete opening of the brace while not being completely separated from the brace.

The main brace body and optional tongue can be constructed from one or more relatively conformable materials such as a layer of foam (for example, open-cell foam). The inside of the main brace body and optional tongue (that is, the part of the main brace body or tongue that is in contact with the skin when the wrist brace is worn) preferably comprises a material that is comfortable against the skin such as polyester or cotton.

A semi-rigid splint is disposed at least partially within the main brace body. The splint is designed to hold the wrist in neutral position when the wrist brace is worn. The splint can comprise any material that is rigid enough to provide support to the hand and wrist but that is conformable to the hand and wrist such that it can accommodate different hand and wrist shapes. Preferably, the splint comprises a semi-rigid metal (for example, aluminum) or plastic.

The splint can be attached to or imbedded within the main brace body using methods known in the art. In some embodiments, the splint is in a pocket created by overlapping main brace body materials and can be removable.

In a preferred embodiment, the semi-rigid splint (preferably, an aluminum splint) is sandwiched between two layers of foam laminates and nylon.

Preferably, the main brace body, or at least a major portion of the main brace body, is breathable (for example, has a moisture vapor transmission rate (MVTR) greater than about 3000 grams per square meter per 24 hours).

Preferably, the outer surfaces of the main brace body are relatively low friction in order to facilitate sliding laces over the surfaces when a lace is tightened or loosened as described below. The low friction surfaces may be formed integrally with the main brace body or may be applied thereto by adhesives, heat bonding, stitching, or the like. The outer surfaces of the main brace body can comprise, for example, spacer fabric, foam laminate, rip-stop nylon, a nylon fabric of 70 denier or higher, or combinations thereof.

Spacer fabric is a laminate that is knitted concurrently. This knitting method provides the ability to manipulate the layers individually to exhibit independent properties. For example, an inner layer can be of a smooth, skin-friendly polyester; a center layer, which is vertical (that is, perpendicular to the inner and outer layers), can be a nylon or monofilament layer that by increasing or decreasing the count per square inch provides more or less density in the overall laminate; and an outer surface can be a nylon to provide wicking of moisture and increased wear resistance. The outer surface of a spacer fabricate visually appears to be porous. Spacer fabricate is available, for example, from Gehring Textiles, Inc. (Garden City, N.Y.) and Eastex Products, Inc. (Holbrook, Mass.).

Rip-stop nylon is a light-weight nylon fabric with interwoven ripstop reinforcement threads in a crosshatch pattern.

In some preferred embodiments, the main brace body comprises a spacer fabric as the primary outer surface. In some preferred embodiments, the inner liner of the main brace body is a urethane foam laminate that provides padding (resilience) against the components of the wrist brace to provide comfort to the user and to avoid pressure points.

The wrist braces of the present invention include an adjustable wrist strap configured to encircle a user's wrist at the bend. As illustrated schematically in FIG. 1, when placed at the bend in the wrist, the strap 10 provides a fulcrum (pivot) between the hand and the forearm. The adjustability of the strap 10 enables the user to fine tune the level of support provided by the strap (that is, the tightness of the strap) as need for a given activity. The hand directs force downward ($F_{hand}$), which in turn applies an upward force at the forearm ($F_{forearm}$). The adjustable wrist strap 10 can be used to change the movement (M) between the wrist and the splint 12 at the bend in the wrist to allow a dynamic (that is, loose) fit up to a nearly completely static fit (that is, a tight fit allowing virtually no movement).

The adjustable wrist strap typically comprises a relatively inelastic material (for example a material having no more than about 15% stretch under tension) such as foam laminates (for example, a laminate including polyester inner layer, urethane foam, and nylon jersey for exterior durability) or a woven nylon strap. The width of the wrist strap can help to distribute the applied circumferential force around the user's wrist so that the support is firm but still comfortable. Typically the wrist strap is between about 2.5 cm and about 5 cm wide. The width of the wrist strap may vary. For example, the wrist strap may be wider at the portion of the strap that is on top of the user's wrist and narrower at the portion that goes around the anterior of the user's wrist.

The adjustable wrist strap can be attached (for example, sewn) to the main brace body at one or more attachment points. For example, the wrist strap may be attached at one of the opposing ends of the main brace body or it may be attached at one or more locations on the anterior of the main brace body.

The adjustability of the wrist strap is provided by a reel and lace system. The reel and lace system includes a lace or cable that is threaded through or otherwise attached to a portion of each end of the wrist strap, and attached at opposite ends to a tightening mechanism as described in further detail below. As used herein, the terms lace and cable have the same meaning unless specified otherwise. The lace is preferably a low friction lace that slides relatively easily through the brace.

The strap tightening lace can, for example, be threaded through a loop at the end of the strap (for example, created by folding over each end of the strap and stitching a loop) on the side of the wrist brace opposite the tightening mechanism. Alternatively, the lace can be threaded through lace guides attached to the end of the wrist strap or near the end of the wrist strap. Lace guides can be attached in any of a variety of ways, as will be appreciated by those of skill in the art. For example, the lace guides can be sewn directly to the wrist strap or main boot assembly. Lace guides can also be inserted into loops created as described above. The lace slides through the loops or lace guides during tightening and untightening of wrist strap as described in more detail below.

Preferably, the lace guides are constructed of rigid materials that resist bending. They are also preferably constructed from low friction materials such as a lubricious polymer or metal that facilitates the sliding of the lace therethrough. Alternatively, the lace guides can be made from any convenient substantially rigid material, and can then be coated with a lubricious coating on at least the sliding portion in order to decrease friction.

Preferably, each of the lace guides defines a pair of openings that communicate with opposite ends of a lumen extending therethrough. The openings are preferably at least as wide as the cross-section of the lumen. Alternatively, the lace guides can comprise an open channel having, for example, a semicircular or "U" shaped cross-section. Examples of lace guides or "guide members" are described in greater detail in U.S. Patent Publication Nos. 2006/0156517 and 2007/0169378.

The lace may be formed from any of a wide variety of polymeric or metal materials or combinations thereof that exhibit sufficient axial strength and bendability for the present application. For example, any of a wide variety of solid core wires, solid core polymers, or multi-filament wires or polymers, which may be woven, braided, twisted or otherwise configured, can be used. A solid or multi-filament metal core can be provided with a polymeric coating such as polytetrafluoroethylene (PTFE) or others known in the art in order to reduce friction. In one embodiment, the lace comprises a stranded cable such as a 7 by 7 strand cable manufactured of stainless steel. In order to reduce friction between the lace and the lace guides through which the lace slid, the outer surface of the lace is preferably coated with a lubricious material such as nylon or PTFE. In a preferred embodiment, the diameter of the lace ranges from about 0.024 inches to about 0.060 inches and is preferably 0.032 inches. The lace is desirably strong enough to withstand loads of at least about 40 pounds and preferably at least about 90 pounds. In certain embodiments, the lace is rated from about 100 pounds up to as high as about 200 pounds or more.

The wrist strap tightening mechanism is mounted to the wrist brace. The tightening mechanism can be located at any variety of locations on the brace. Typically it is located on the posterior of the wrist brace on the opposing side closest to the thumb. Location of the wrist strap tightening mechanism may be optimized in view of a variety of considerations including overall brace design. The shape and overall volume of the wrist strap tightening mechanism can be varied depending, for example, upon the gear train design. A relatively low-profile wrist strap tightening mechanism is generally preferred. The mounted profile of the wrist strap tightening mechanism can be further reduced by recessing the tightening mechanism into the outer surface of the brace.

In general, the wrist strap tightening mechanism comprises a control such as a lever, crank or knob, which can be manipulated to retract the lace. In addition, the wrist strap tightening mechanism preferably comprises a mechanism of release such as a button or lever for disengaging the wrist strap tightening mechanism to permit the lace to be withdrawn freely. In some embodiments, the wrist strap tightening mechanism is released by pulling outwards on the control or by rotating the control knob counterclockwise. In some embodiments, an additional lock may be provided in the form of, for example, a button or lever that must be actuated to allow the control to be, for example, pulled outwards to release the system.

The wrist strap tightening mechanism generally comprises a housing and a circular knob rotatably mounted thereto. The knob may be rotated to wind the end of the lace into the housing and thereby provide the final tension to the lace to reduce the slack and provide the desired level of tightness. As the slack in the lace reduces, the lace pulls the opposing edges of the wrist strap toward each other, tightening the wrist strap to provide more support to the wearer. The knob may also be rotated through the use of a tool or small motor attached to the knob. Examples of various tightening mechanisms suitable for this task are disclosed in greater detail in U.S. Patent Publication Nos. 2006/0156517 and 2007/0169378. Suitable tightening mechanisms are available from Boa Technology, Inc. (Steamboat Springs, Colo.).

Preferably, one or more additional lacing systems and tightening mechanisms are provided to tighten the main brace body or portions of the main brace body of the wrist brace. For example, one additional lacing system and tightening mechanism may be utilized to tighten the portion of the main brace body above the wrist strap (that is, the portion on the hand) and another additional lacing system and tightening mechanism may be utilized to tighten the portion of the main brace body below the wrist strap (that is, the portion on the forearm).

In such embodiments, a lace can be threaded through a lacing guide on the opposing side of the main brace body. The lace may be threaded in a crossing pattern along a forward-facing portion of the brace between two generally parallel rows of side retaining guide members. A crossing pattern is not required, however. The number of retaining guide members may vary. Preferably, the lace slides through guides on the tongue of the brace and maintains a connection between the tongue and the main brace body when the brace is in its open configuration.

Figure 2:
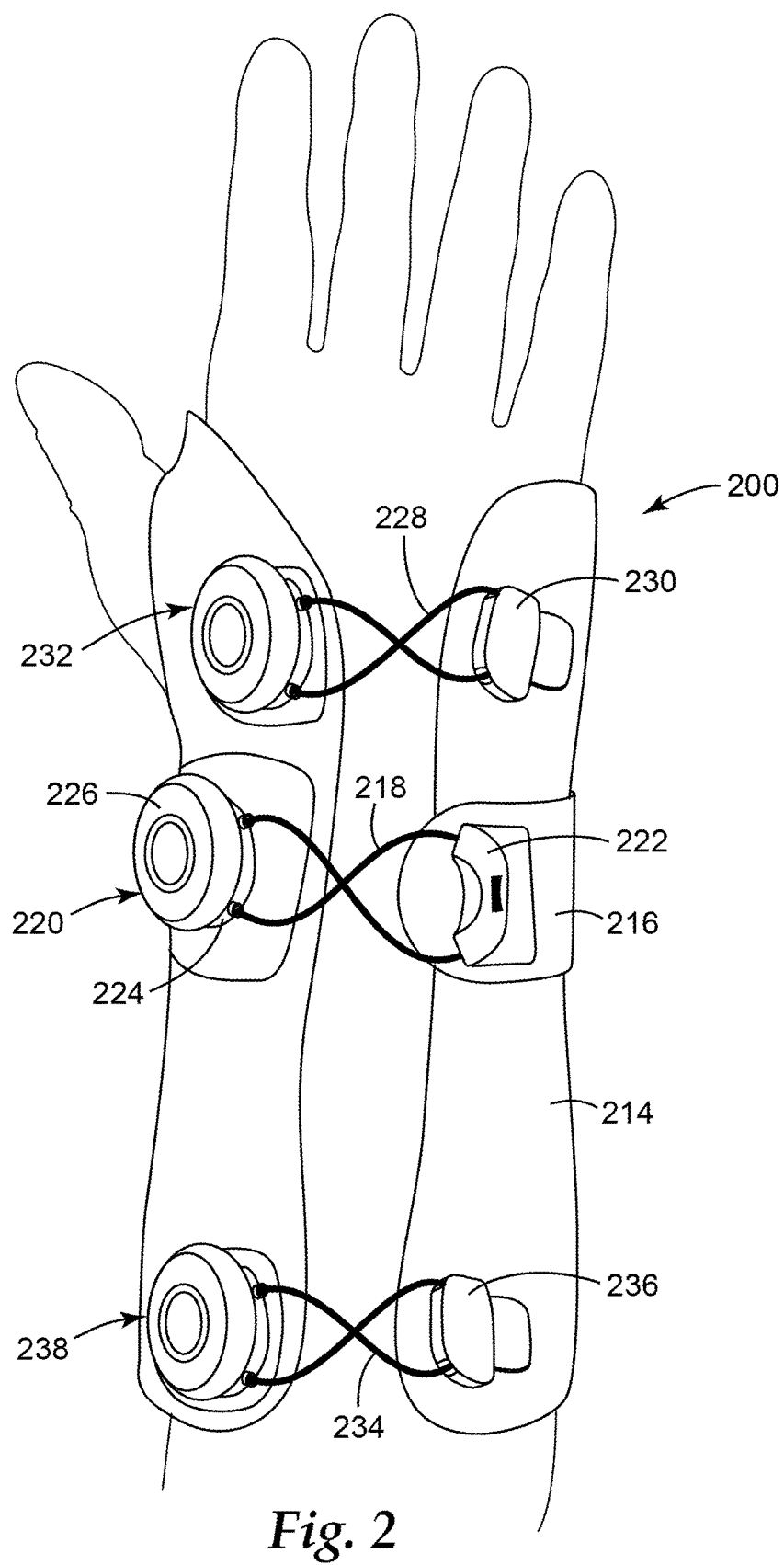
FIG. 2 is a schematic representation of an embodiment of the wrist brace of the invention.

FIG. 2 illustrates a wrist brace of the invention that has one lacing system and tightening mechanism for tightening the upper portion of the brace, one lacing system and tightening mechanism for the wrist strap, and one lacing system and tightening mechanism for the lower portion of the brace.

Wrist brace 200 comprises main brace body 214 with a semi-rigid splint disposed therein (not shown). Adjustable wrist strap 216 is attached to main brace body 214 and is configured to encircle main brace body 214 about a wearer's wrist. The adjustability of wrist strap 216 is provided by a reel and lace system that includes lace 218 and tightening mechanism 220. Lace 218 is attached at opposite ends to tightening mechanism 220 and is threaded in a crossing pattern along a forward facing portion of the brace through lace guide 222. Tightening mechanism 220 is mounted to main brace body 214 through adjustable wrist strap 216. Tightening mechanism 220 comprises housing 224 and circular knob 226 mounted thereto.

A separate lacing system and tightening mechanism is utilized to tighten the upper portion of wrist brace 200 (that is, the portion of the brace that is on the hand when worn). A second lace 228 is threaded through upper lacing guide 230 on the upper portion of main brace body 214 and attached at opposite ends to upper tightening mechanism 232 located above tightening mechanism 220.

A third lacing system and tightening mechanism is utilized to tighten the lower portion of wrist brace 200 (that is, the portion of the brace that is on the forearm when worn). A third lace 234 is threaded through lower lacing guide 236 on the lower portion of main brace body 214 and attached at opposite ends to lower tightening mechanism 238 located below tightening mechanism 220.

Figure 3:
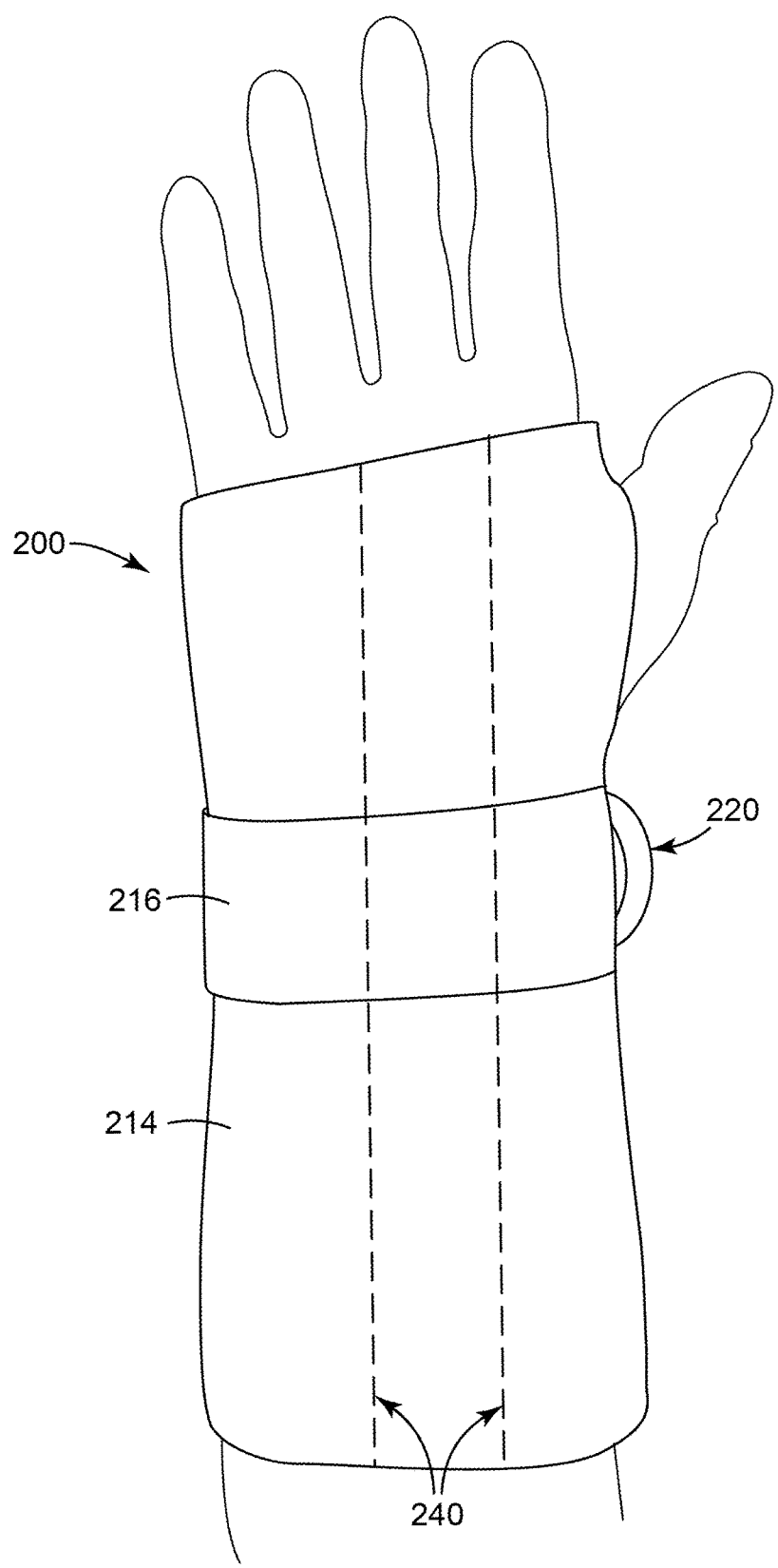
FIG. 3 is a schematic representation of an alternative view of the wrist brace illustrated in FIG. 2.

FIG. 3 shows the anterior side of wrist brace 200. Adjustable wrist strap 216 encircles main brace body 214 about the wearer's wrist. Adjustable wrist strap 216 is attached to main brace body 214 by two seams 240.

The laces do not have to be threaded in a crossing pattern in the lacing zone. As will be apparent to those of skill in the art, it is possible to configure the lacing system such that the lace passes across the outer surface of the brace in a substantially parallel, uncrossed path. Such substantially parallel lacing configurations are disclosed in greater detail in U.S. Pat. No. 8,277,401.

Figure 4:
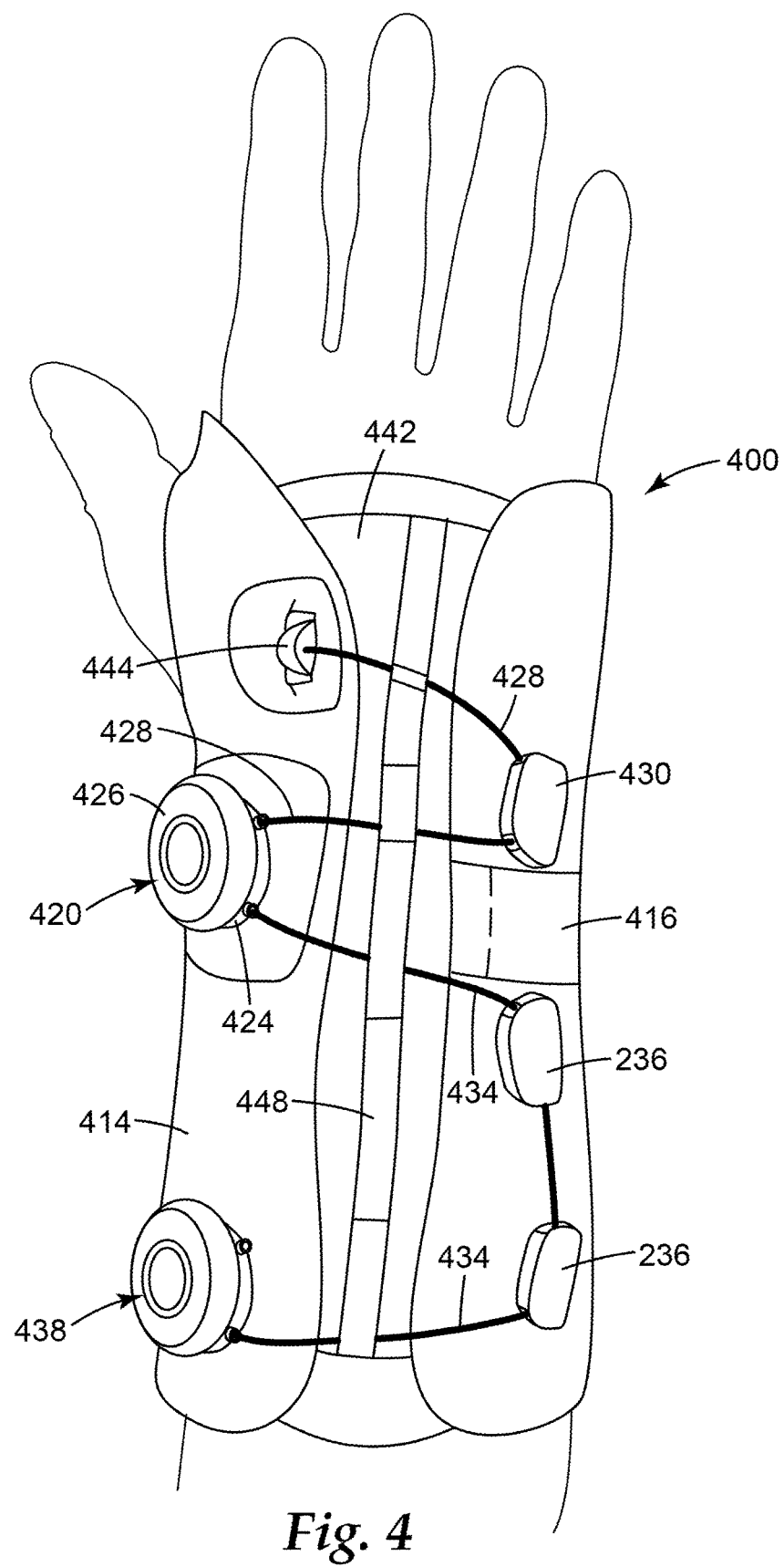
FIG. 4 is a schematic representation of another embodiment of a wrist brace.

FIG. 4 illustrates a wrist brace that has one lacing system and tightening mechanism for tightening the upper portion of the brace, one lacing system lacing system and tightening mechanism for the lower portion of the brace.

Wrist brace 400 comprises main brace body 414 with a semi-rigid splint disposed therein (not shown) and tongue portion 442. Adjustable wrist strap 416 is attached to main brace body 414 and is configured to encircle main brace body 414 about a wearer's wrist.

The adjustability of wrist brace 400 is provided by two reel and lace systems. A first lacing system and tightening mechanism is utilized to tighten the upper portion of wrist brace 400 from wrist strap 416 through the portion of main brace body 414 that is on the hand when worn. This first lacing/tightening system includes lace 428, which is attached at one end to tightening mechanism 420 and at the opposite end to lace retainer 444, is threaded along a forward facing portion of the brace through upper lacing guide 430 on the upper portion of main brace body 414. Tightening mechanism 420 is mounted to main brace body 414 through adjustable wrist strap 416. Tightening mechanism 420 comprises housing 424 and circular knob 426 mounted thereto.

A second lacing system and tightening mechanism is utilized to tighten the lower portion of wrist brace 400 from wrist strap 416 through the portion of the main brace body 414 that is on the forearm when worn. This second lacing/tightening system includes lace 434, which is attached at one end to tightening mechanism 420 and at the opposite end to tightening mechanism 438, is threaded along a forward facing portion of the brace through two lower lacing guides 236 on the lower portion of main brace body 416.

Laces 428 and 434 slide through tongue lace guide 448 on tongue portion 442 and maintain a connection between tongue portion 442 and main brace body 414 when brace 400 is in open configuration.

When wrist braces comprise two or more separate tightening mechanisms, the wearer may tighten certain portions of the brace more than others. That is, the brace is capable of zonal tightening wherein different zones may have different tightness. Examples of zonal tightening are described in greater detail in U.S. Patent Publication No. 2006/0156517.

In some embodiments, the guides placed in the middle of the brace near or on the wrist strap include a shorter distance between the openings than is used in guides higher up on the brace (that is, close to the fingers) or lower down on the brace (that is, on the forearm). This shorter distance increases the closing force in the area around the pivot point of the wrist.

The complete disclosures of the publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

I claim:

1. A wrist brace comprising:
    a main brace body comprising a semi-rigid splint configured to fit the anterior of a wearer's wrist, the splint configured to extend from the palm to a portion of the anterior of the forearm and disposed at least partially within the main brace body, wherein the main brace body comprises first and second opposing sides that, during use, are drawn towards each other on the posterior of the wearer's wrist and forearm, the opposing sides each having an upper portion and a lower portion;
    a first tightening system disposed on an upper portion of the main brace body for tightening the upper portions, the first tightening system comprising a first lace, a first lace guide, a first rotatable tightening mechanism, and a lace retainer mounted to the brace body, wherein the first lace guide is disposed on a side of the brace body opposite the first rotatable tightening mechanism and lace retainer; and
    a second tightening system disposed on a portion of the main brace body proximal to the first tightening system for tightening the lower portions, the second tightening system comprising a second lace, a second lace guide, and a second rotatable tightening mechanism, wherein the second tightening system further comprises a third lace guide disposed on the main brace body proximal to the second lace guide, and wherein the second and third lace guides are disposed on a side of the brace body opposite the second rotatable tightening mechanism; wherein the second lace is threaded through both the second and third lace guides and is secured to both the first and second rotatable tightening mechanisms, such that when the second rotatable tightening mechanism applies tension on the second lace, the lower portions are advanced towards each other.

2. The wrist brace of claim 1, wherein each tightening mechanism and the lace retainer are disposed on the first side of the main brace body, and wherein the lace guides are disposed on the second side of the main body.

3. The wrist brace of claim 1, wherein the first rotatable tightening mechanism is disposed on the first side of the main brace body at a location between the first lacing guide and the second lacing guide.

4. The wrist brace of claim 1, wherein the first lace is threaded through the first lace guide, is secured at one end to the first tightening mechanism and secured at another end to the lace retainer, such that when the first rotatable tightening mechanism applies tension on the first lace, the upper portions are advanced towards each other.

5. The wrist brace of claim 1, wherein the main brace body includes a defined receptacle, and wherein the splint is received in the receptacle.

6. The wrist brace of claim 5, wherein the main brace body includes a defined pocket, and wherein the splint is received in the pocket.

7. The wrist brace of claim 1, wherein the splint is removable.

8. The wrist brace of claim 1, wherein the splint is disposed only on the anterior of the wearer's wrist during use.

9. The wrist brace of claim 1 and further comprising a tongue configured to be positioned beneath and between the opposing sides of the main brace body when the wrist brace is closed.

10. The wrist brace of claim 1 wherein the main brace body comprises a combination of foam laminate and spacer fabric as the primary outer surface.

11. The wrist brace of claim 1, wherein the tightening mechanism comprises a mechanism of release for disengaging the tightening mechanism.

12. The wrist brace of claim 1, wherein the splint comprises aluminum.

13. The wrist brace of claim 1, wherein the main brace body comprises a spacer fabric as a primary outer surface.

14. The wrist brace of claim 1 wherein the main brace body comprises rip-stop nylon as the primary outer surface.

15. The wrist brace of claim 1, wherein the main brace body comprises a nylon fabric of 70 denier or higher as a primary outer surface.

* * * * *